US012770311B2

(12) United States Patent
Chang et al.

(10) Patent No.: US 12,770,311 B2
(45) Date of Patent: Oct. 20, 2026

(54) METHOD FOR REDUCING METAL ARTIFACTS IN CT IMAGES

(71) Applicant: National Atomic Research Institute, Taoyuan (TW)

(72) Inventors: Chia-Hao Chang, Taoyuan (TW); Hsiang-Ning Wu, Taoyuan (TW)

(73) Assignee: National Atomic Research institute, Taoyuan (TW)

( * ) Notice: Subject to any disclaimer, the term of this patent is extended or adjusted under 35 U.S.C. 154(b) by 313 days.

(21) Appl. No.: 18/600,845

(22) Filed: Mar. 11, 2024

(65) Prior Publication Data

US 2025/0272891 A1 Aug. 28, 2025

(30) Foreign Application Priority Data

Feb. 27, 2024 (TW) ................................ 113107028

(51) Int. Cl.
*A61B 6/58* (2024.01)
*A61B 6/00* (2006.01)
(Continued)

(52) U.S. Cl.
CPC .............. *G06T 12/30* (2026.01); *A61B 6/032* (2013.01); *A61B 6/5258* (2013.01); *A61B 6/583* (2013.01);
(Continued)

(58) Field of Classification Search
CPC ....... G06T 12/30; G06T 7/0012; G06T 12/10; G06T 2207/10081; G06T 2207/30012;
(Continued)

(56) References Cited

U.S. PATENT DOCUMENTS

2024/0233213 A1* 7/2024 Qiang .................... A61B 6/037

FOREIGN PATENT DOCUMENTS

WO WO-2021108715 A1 * 6/2021 ............... A61B 6/54
WO WO-2023044114 A1 * 3/2023 ............ G06T 12/10

OTHER PUBLICATIONS

Frederic et al. "An Efficient One-Step Method for Spectral CT Based on an Approximate Linear Model", IEEE Transactions on Radiation and Plasma Medical Sciences, vol. 5, No. 4, Jul. 2021, p. 528-536. (Year: 2021).*

(Continued)

*Primary Examiner* — Uzma Alam
*Assistant Examiner* — Mamadou Faye
(74) *Attorney, Agent, or Firm* — Troutman Pepper Locke LLP; Tim Tingkang Xia, Esq.

(57) ABSTRACT

A method for reducing metal artifacts in CT images, including the following steps: a material decomposition (MD) calibration step, using multiple MD calibration phantoms with known characteristics and multiple spectral CT data corresponding thereto to construct a system characteristic model of spectral CT; and a MD testing step, including: the following steps: imaging multiple testing objects with a different unknown material and thickness to obtain projection-based multiple spectral CT imaging data of different energy bins; obtaining corresponding multiple basis material images of different materials based on projection data according to the spectral CT imaging data and the system characteristic model of spectral CT; and combining the basis material images and a photon energy information to be recombined with each other to obtain multiple virtual mono-energetic images.

8 Claims, 5 Drawing Sheets

(51) Int. Cl.
*A61B 6/03* (2006.01)
*G06T 12/10* (2026.01)
*G06T 12/30* (2026.01)

(52) U.S. Cl.
CPC .... *G06T 12/10* (2026.01); *G06T 2207/10081* (2013.01); *G06T 2207/30012* (2013.01); *G06T 2207/30036* (2013.01); *G06T 2210/41* (2013.01); *G06T 2211/408* (2013.01); *G06T 2211/448* (2023.08)

(58) Field of Classification Search
CPC ....... G06T 2207/30036; G06T 2210/41; G06T 2211/448; G06T 2211/408; A61B 6/5258; A61B 6/583; A61B 6/032
See application file for complete search history.

(56) References Cited

OTHER PUBLICATIONS

Chia-Hao Chang et al., Virtual monochromatic imaging with projection-based material decomposition algorithm for metal artifacts reduction in photon-counting detector computed tomography, PLoS One, 2023.

* cited by examiner

METHOD FOR REDUCING METAL ARTIFACTS IN CT IMAGES

CROSS REFERENCE TO RELATED APPLICATION

All related applications are incorporated by reference. The present application is based on, and claims priority from, Taiwan Application Serial Number 113107028, filed on Feb. 27, 2024, the disclosure of which is hereby incorporated by reference herein in its entirety.

TECHNICAL FIELD

The present disclosure relates to a method for reducing metal artifacts in CT images, and more particularly to an algorithm used in a spectral computed tomography imaging system to generate a virtual monoenergetic image (VMI), and an image processing method for reducing metal artifacts in CT images.

BACKGROUND

Computed tomography (CT) can provide high-resolution three-dimensional structural image information of the interior of the object to be tested (such as the human body or industrial parts, etc.) and is currently very important one of the detection tools in the field of medical diagnosis or industrial non-destructive testing.

However, whether it is artificial implants for medical diagnosis (such as hip prostheses, bone screws, or dental fillings, etc.) or high-attenuation materials such as metal parts for industrial inspection, serious metal artifacts will occur during the CT imaging process, and these metal artifacts will not only blur the image of the high-attenuation material area, but also interfere with the normal tissue areas around the high-attenuation material area, reducing the diagnosis or inspection performance of medical diagnosis or industrial detection. Therefore, how to reduce or suppress the metal artifact problem in CT images is one of the research issues to be solved in the field of CT imaging.

Existing technologies for suppressing CT metal artifacts are mainly methods based on sinogram painting, such as linear interpolation metal artifacts reduction (LMAR) or normalization metal artifacts reduction (NMAR), mainly separating the high-attenuation material areas that cause metal artifacts from the normal tissue areas in the sinogram of the original CT data, and filling the high-attenuation material areas with lower values, and merging it back into the original sinogram for numerical normalization or interpolation. Furthermore, the CT image reconstruction algorithm is used to obtain the image of the area without high attenuation material to achieve the purpose of reducing CT metal artifacts. However, the disadvantage of this method is that it causes blurring of some images around high-attenuation material areas, and if it occurs in critical tissues and organs, the impact will be more serious.

SUMMARY

The embodiments of the present disclosure provide a method for reducing metal artifacts in CT images, capable of improving the quality of spectral computed tomography (CT) images.

The present disclosure, in an embodiment, proposes a

In an embodiment of the present invention, the above-mentioned material decomposition (MD) calibration step includes the following steps: using multiple reference materials with known characteristics as the MD calibration phantoms; and imaging the MD calibration phantoms with a different material and thickness to obtain the spectral CT calibration data of different energy bins based on projection corresponding to the MD calibration phantoms with a different material and thickness.

In an embodiment, the present disclosure further including the following step: placing the MD calibration phantoms between an X-ray tube and a photon-counting detector in the step of imaging the MD calibration phantoms with a different material and thickness.

In an embodiment, the present disclosure further includes the following steps: using the MD calibration phantoms as an input end of the system characteristic model of spectral CT; using the spectral CT calibration data as an output end of the system characteristic model of spectral CT; and constructing the system characteristic model of spectral CT related to both the MD calibration phantoms and the spectral CT calibration data after the step of imaging the MD calibration phantoms with a different material and thickness.

In an embodiment, the present disclosure further includes the following step: substituting the MD calibration phantoms together with the spectral CT calibration data corresponding thereto into a MD calibration algorithm to construct the system characteristic model of spectral CT in the step of constructing the system characteristic model of spectral CT related to both the MD calibration phantoms and the spectral CT calibration data.

In an embodiment, the pressure disclosure further includes the following step: using a polynomial approximation method as the MD calibration algorithm in the step of substituting the MD calibration phantoms together with the spectral CT calibration data corresponding thereto into the MD calibration algorithm.

In an embodiment, the present disclosure further includes the following steps: adopting a maximum likelihood estimation method (MLEM) to estimate a calculated thickness of MD calibration phantom; and using an error calibration look-up table (LUT) to calibrate the MD calibration phantom thickness to obtain a material thickness estimation a calibration parameter for material calibration estimation in the system characteristic model of spectral CT in the step of substituting the MD calibration phantoms together with the spectral CT calibration data corresponding thereto into the MD calibration algorithm.

In an embodiment, the present disclosure further including the following step: substituting the spectral CT imaging data and the system characteristic model of spectral CT into a basis MD algorithm in the step of obtaining corresponding multiple basis material images of different materials based on projection data according to the spectral CT imaging data and the system characteristic model of spectral CT.

In an embodiment, the present disclosure further including the following step: image-reconstructing the virtual monoenergetic image based on projection to obtain a three-dimensional CT reconstruction image after the step of obtain the virtual monoenergetic image.

Based on the above, the method for reducing metal artifacts in CT images of the present disclosure can generate the virtual monoenergetic CT images of a specific energy (such as synchrotron radiation) through projection-based MD data of spectral CT and the monoenergetic image photon energy information to be obtained, capable of reducing the metal artifacts in CT images.

Furthermore, the present disclosure generates virtual monoenergetic images to reduce metal artifacts based on projection domain by means of image recombination rather than simply by means of image post-processing, which not only can effectively reduce metal artifacts, but can maintain normal tissue image structure information around high-attenuation material area.

In addition, the present disclosure can generate virtual monoenergetic CT images, and the pixel value in the image represents the attenuation coefficient of a specific energy photon (for example: 100 keV) in a certain area, thereby capable of more accurately representing the characteristics of the material in the area, which can improve the accuracy of image quantification.

In order to make the present disclosure more obvious and understandable, embodiments are given below, and detailed descriptions are given below with reference to the attached drawings.

DETAILED DESCRIPTION

The following embodiments are enumerated and described in detail with reference to the accompanying drawings. However, the provided embodiments are not intended to limit the scope of the present disclosure. In addition, the drawings are for illustrative purposes only and are not drawn to original size. To facilitate understanding, the same elements will be identified with the same symbols in the following description.

The terms “including”, “comprising”, “having”, etc. mentioned in this disclosure are all open terms, that is, they mean “including but not limited to”.

In the description of each embodiment, when terms such as “first”, “second”, “third”, “fourth”, etc. are used to describe elements, they are only used to distinguish these elements from each other, and There is no restriction on the order or importance of these elements.

In the description of various embodiments, the so-called “coupling” or “connection” may refer to two or more components making direct physical or electrical contact with each other, or indirectly making physical or electrical contact with each other. “Coupling” or “connection” can also refer to the mutual operation or action of two or more components.

Figure 1:
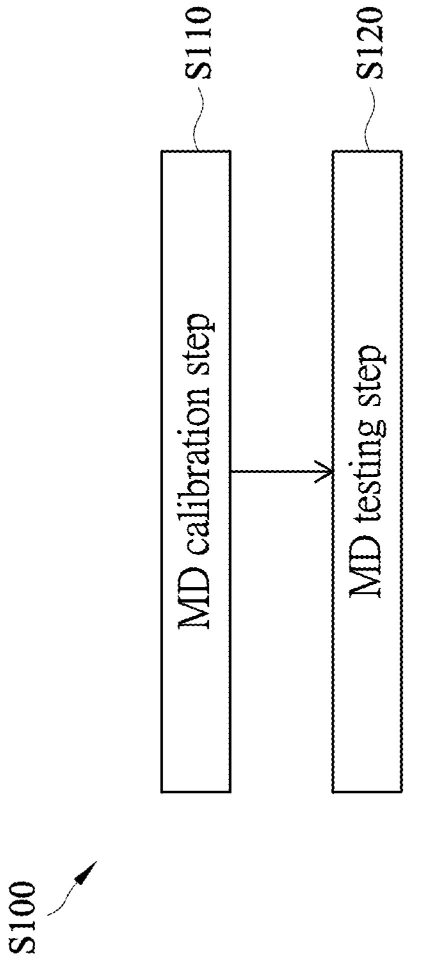
FIG. 1 is a flow chart of a method for reducing metal artifacts in CT images according to the present disclosure.

FIG. 1 is a flow chart of a method for reducing metal artifacts in CT images according to the present disclosure. Referring to FIG. 1, a method S100 for reducing metal artifacts in CT images of the present disclosure can effectively suppress metal artifacts in CT images, and includes two stages: step S110 and step S120, where step S110 is a MD calibration step, and S120 is a MD testing step.

The first stage: step S110 is MD calibration step, using multiple MD calibration phantoms with known characteristics and the spectral CT calibration data corresponding thereto to construct a system characteristic model of spectral CT.

In detail, the MD calibration step S110 includes the following steps: first, using a reference material with various known characteristics (such as known material and thickness) as a MD calibration phantom. Since the material and thickness of the reference material with these known characteristics, and the attenuation coefficient are known, the reference material with the known characteristics is used as a MD calibration phantom to use as an output end of the system characteristic model of spectral CT, where the attenuation coefficient is related to the material of the object and the photon energy.

Next, these MD calibration phantoms with a different material and thickness combination are imaged to obtain spectral CT calibration data of different material and thickness combinations. The spectral CT imaging system 100 shown in FIG. 2 includes an X-ray tube 110 and a photon-counting detector (PCD) 120, and an object 50 such as the above MD calibration phantom is placed between the X-ray tube 110 and the photon-counting detector 120. The spectral CT calibration data is obtained through the X-ray tube 110 and the photon-counting detector 120, allowing these MD calibration phantoms with a different material and thickness combination to have spectral CT calibration data of different energy bins based on projection corresponding thereto.

Next, a system characteristic model of spectral CT in relation with the MD calibration phantoms and spectral CT calibration data is constructed, where these MD calibration phantoms are used as an input end of the system characteristic model of spectral CT, and the spectral CT calibration data is used as an output end of the system spectral model of spectral CT, allowing the material, thickness and projection data (spectral CT calibration data) of the MD calibration phantoms to have a certain relationship to obtain the system characteristic model of spectral CT. The purpose of the system characteristic model of spectral CT is to convert the imaging data of a testing object with unknown material and thickness and its projection to obtain information related to the equivalent thickness of the basis materials.

For example, these MD calibration phantoms are substituted into MD calibration algorithm together with their corresponding spectral CT calibration data. In an embodiment, a polynomial approximation method is used as the MD calibration algorithm. The system characteristic model of spectral CT may be expanded and through Taylor expansion and expressed by polynomial approximation such as mathematical formula (1) and mathematical formula (2), where $P_1$ and $P_2$ represent the projection data of two different energy bins for spectral CT, $A_{m1}$ and $A_{m2}$ represent the thicknesses of the MD calibration phantoms of two different energy bins, and $c_{11}$ to $c_{16}$, $C_{21}$ to $C_{26}$ are unknown coefficients.

$$P_1 = c_{11} + c_{12}A_{m1} + c_{13}A_{m2} + c_{14}A_{m1}^2 + c_{15}A_{m1}A_{m2} + c_{16}A_{m2}^2; \quad (1)$$

$$P_2 = c_{21} + c_{22}A_{m1} + c_{23}A_{m2} + c_{24}A_{m1}^2 + c_{25}A_{m1}A_{m2} + c_{26}A_{m2}^2;. \quad (2)$$

In another embodiment, the MD calibration algorithm uses the maximum likelihood estimation (MLE) method having an error calibration look-up table (LUT). The maximum likelihood estimation method is used to estimate a calculated thickness of the MD calibration phantom, so as to establish the system characteristic model of spectral CT. The MD calibration phantom thickness calculation value estimated by the maximum likelihood estimation method is an approximation. Next, the error calibration look-up table is used to carry out the action of lookup calibration, so as to calibrate the MD calibration phantom thickness calculation value and obtain the calibration parameters of the material thickness estimation in the system characteristic model of spectral CT, thereby reducing the approximation error calculated by the maximum likelihood estimation method.

Figure 3:
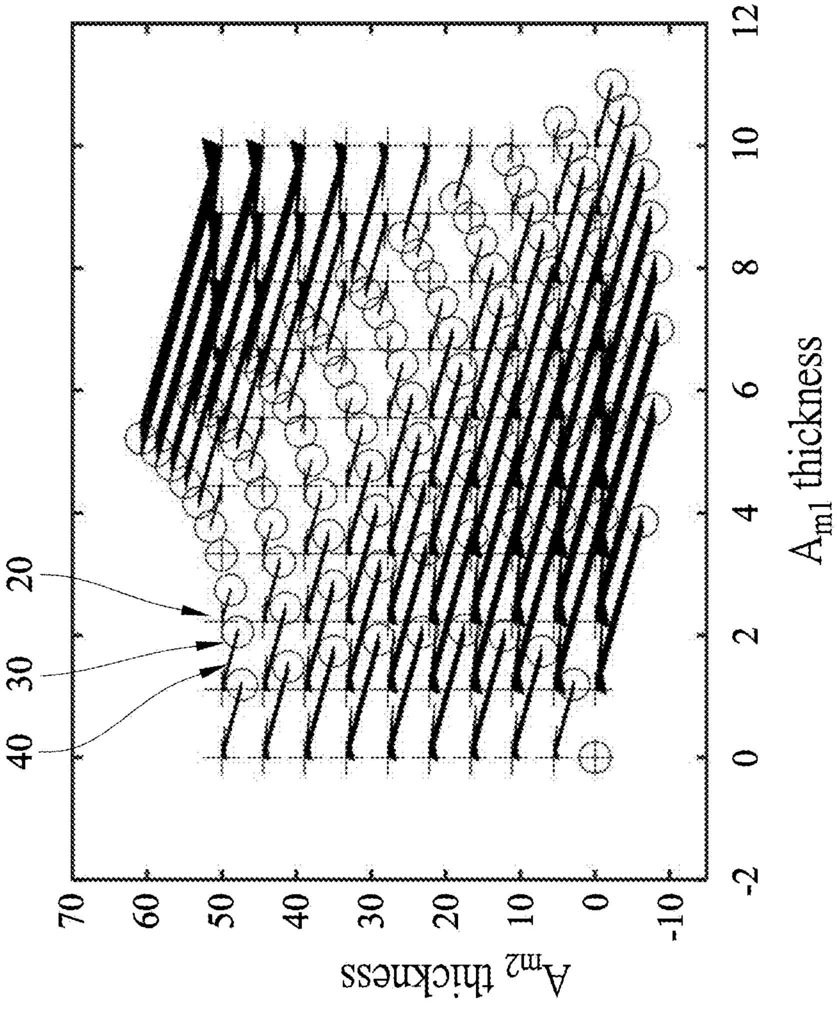
FIG. 3 is a schematic view of an embodiment of an error calibration look-up table according to the present disclosure.

The error calibration look-up table is shown in FIG. 3, where the horizontal axis is the thickness $A_{m1}$, which represents the thickness of material m1, and the vertical axis is the thickness $A_{m2}$, which represents the thickness of material m2. The cross mark 20 is the thickness of the MD calibration phantom, which is the nominal thickness value of the MD calibration phantom, the round mark 30 is the calculated thickness value of the MD calibration phantom, and the arrow 40 represents the thickness error correction vector, where the thickness of the MD calibration phantom is equal to the sum of the calculated thickness value of the MD calibration phantom and the value of the thickness error correction vector.

Figure 2:
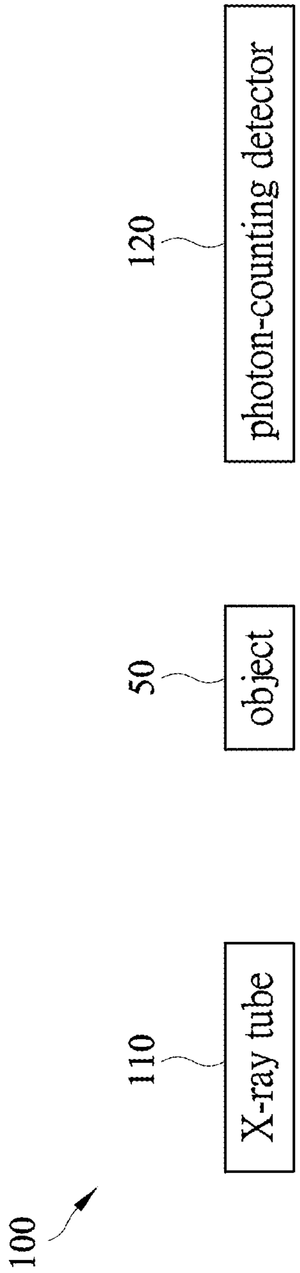
FIG. 2 is a schematic view of an embodiment of a spectral CT imaging system according to the present disclosure.

After step S110 is completed, step S120 is then carried out; step S120 is the MD testing process, including the following steps: first, imaging multiple testing objects with a different unknown material and thickness to obtain projection-based spectral CT imaging data of different energy bins. As shown in FIG. 2, the projection-based spectral CT of different energy bins is obtained, the testing objects are used as the object 50 and placed in the spectral CT imaging system 100 as shown in FIG. 2 for imaging to obtain the projection-based spectral CT imaging data of different energy bins.

Next, the corresponding basis material projections of different materials based on the projection data are obtained according to these spectral CT imaging data of different energy bins and the system characteristic model of spectral CT obtained in the above step S110. For example, these spectral CT imaging data of different energy bins and the system characteristic model of spectral CT obtained in the above step S110 are substituted into a projection-based basis material decomposition algorithm (basis MD algorithm), as shown in the mathematical formula (3), $A_{MLE}$ is the calculation value of the thickness of the MD testing phantom, which is the calculation value of the thickness of the MD testing phantom estimated through the maximum likelihood estimation method, P projection array is spectral CT imaging data, $R_{P|A}$ is a covariance array of the P projection array; array M is related to the system characteristic model of spectral CT, which is obtained by the thickness of the MD calibration and the spectral CT calibration data. It can be known from the mathematical formula (3) that the projection-based data are parameters having the system characteristic model of spectral CT in the basis MD algorithm.

$$A_{MLE} = \left(M^T R_{P|A}^{-1} M\right)^{-1} M^T R_{P|A}^{-1} P. \quad (3)$$

Based on this, the corresponding basis material projections of two different material based on projection data are obtained after the spectral CT imaging data of two different energy bins are calculated through the basis MD algorithm by means of the projection-based material decomposition of spectral CT, achieving the purpose of material decomposition.

Next, these basis material projections are combined with the photon energy information to be recombined (the attenuation coefficient of a specific photon energy) to obtain a virtual monoenergetic image (VMI). Since the basis material projection includes the information about materials and attenuation coefficients, these basis material projections can be combined together to construct a virtual monoenergetic image of a specific energy bin. The present disclosure uses the different energy-bin signal of the photon-counting detector to calculate the virtual monoenergetic image, and as shown in mathematical formula (4), where $E_{VMI}$ is the specific photon energy; $A_{m1}$ and $A_{m2}$ are the thicknesses of material m1 and material m2; $\mu_{m1}$ and $\mu_{m2}$ are the attenuation coefficients of material m1 and material m2.

$$P(E_{VMI}) = \mu_{m1}(E_{VMI}) \cdot A_{m1} + \mu_{m2}(E_{VMI}) \cdot A_{m2}. \quad (4)$$

Next, these above-mentioned virtual monoenergetic images based on projection are image-reconstructed to obtain three-dimensional CT reconstructed images.

Figure 4A:
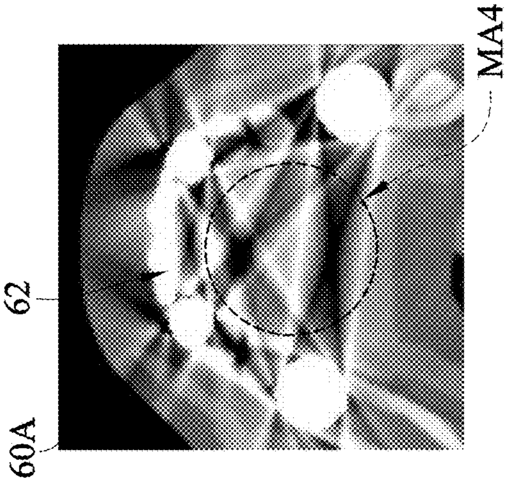
FIGS. 4A to 4D respectively are a contrast image for medical dental fillings.
Figure 4B:
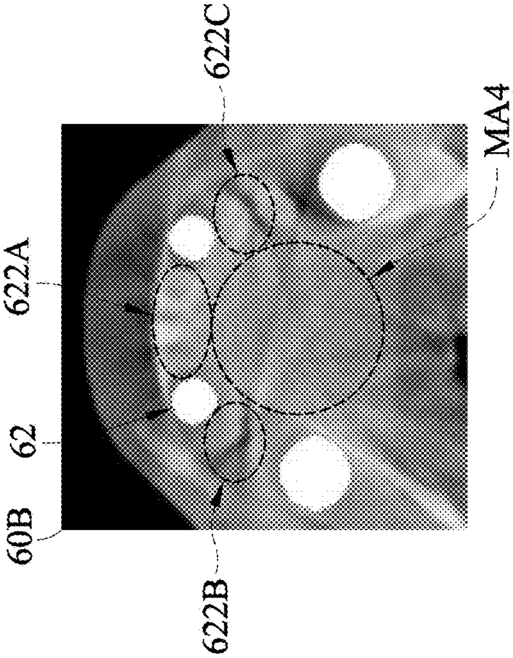
Figure 4C:
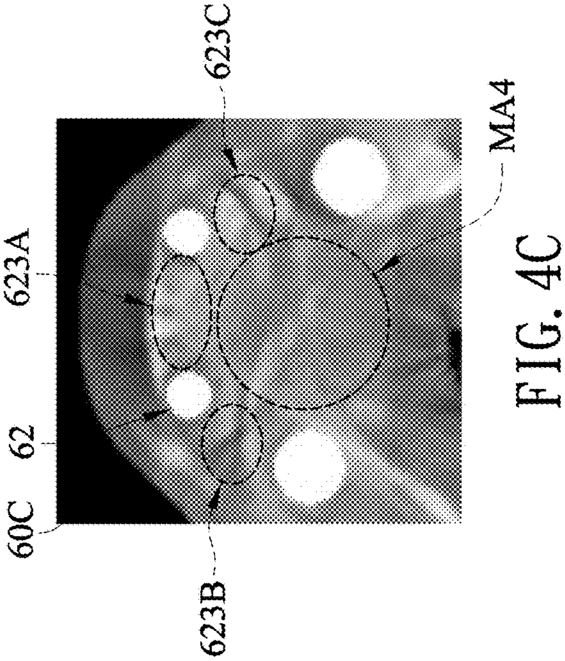

FIGS. 4A to 4D respectively are a contrast image for medical dental fillings, where FIG. 4A shows the traditional CT image 60A of medical dental fillings imaging. A part of area of the denture 62 of the traditional CT image 60A and its inner area MA4 have metal artifacts. FIGS. 4B and 4C respectively show a first metal artifact removal image 60B and a second metal artifact removal image 60C formed by using linear interpolation metal artifact removal method (LMAR) and normalized metal artifact removal method (NMAR) to remove metal artifacts. It can be seen from both FIGS. 4B and 4C that LMAR and NMAR use the image post-processing method to effectively remove the metal artifacts in the inner area MA4 of the first metal artifact removal image 60B and the inner area MA4 of the second metal artifact removal image 60C (compared to FIG. 4A), but it affects the normal tissue structure of the image around the inner area MA4, such as the areas around the dentures 622A, 622B, and 622C in FIG. 4B, or the areas around the dentures 623A, 623B, and 623C in FIG. 4C.

Figure 4D:
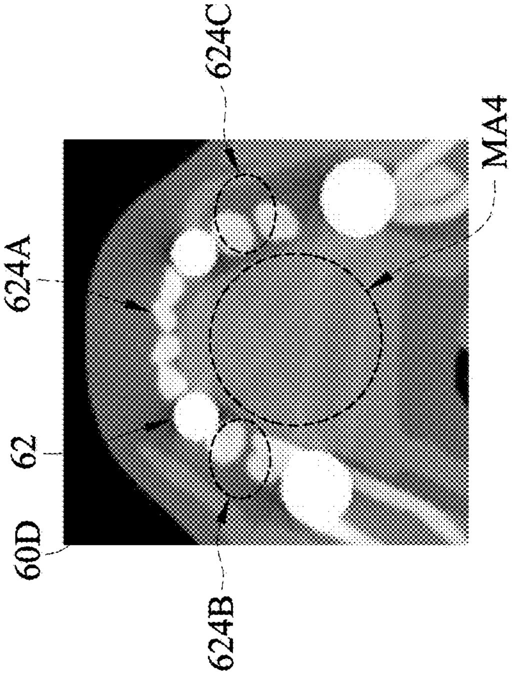

On the other hand, as shown in FIG. 4D, it shows a virtual monoenergetic image 60D imaged by the method S100 of the present disclosure for reducing metal artifacts in CT images. It not only effectively removes the metal artifacts in a part of area of the denture 62 and its inner area MA4, but compared to FIGS. 4B and 4C, the areas 624A, 624B, and 624C around the denture in the denture 62 are all retained without being removed, which can maintain the normal tissue structure of the image around the high-attenuation material without being affected by metal artifacts, capable of improving the quality of spectral CT images.

Figure 5A:
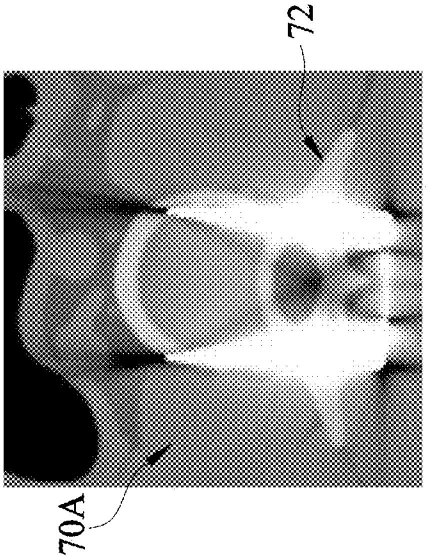
FIGS. 5A to 5D respectively are a contrast image for lumbar spine with bone screws.
Figure 5B:
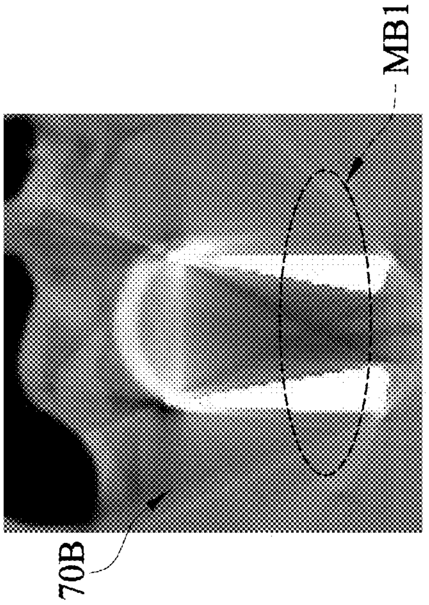
Figure 5C:
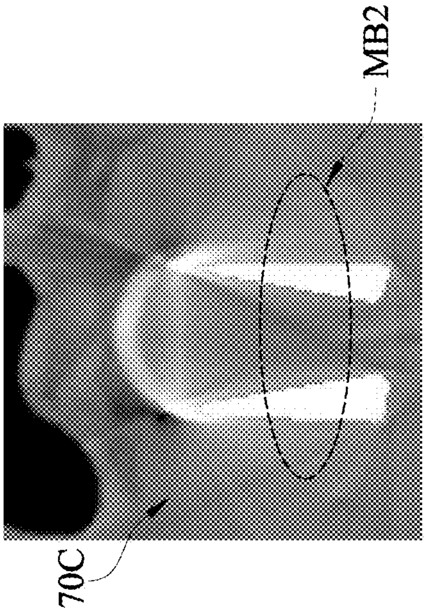

Similarly, FIGS. 5A to 5D respectively are a contrast image for lumbar spine with bone screws, where FIG. 5A shows the traditional CT image 70A of lumbar spine with bone screws imaging. The lumbar spine with bone screws area 72 has metal artifacts. FIGS. 5B and 5C respectively show a first metal artifact removal image 70B and a second metal artifact removal image 70C formed by using linear interpolation metal artifact removal method (LMAR) and normalized metal artifact removal method (NMAR) to remove metal artifacts. It can be seen from both FIGS. 5B and 5C that the artifact area MB1 of the first metal artifact removal image 70B and the artifact area MB2 of the second metal artifact removal image 70C are effectively removed (compared to FIG. 5A), but the normal tissue structures of the image around the artifact areas MB1 and MB2 are also removed at the same time.

Figure 5D:
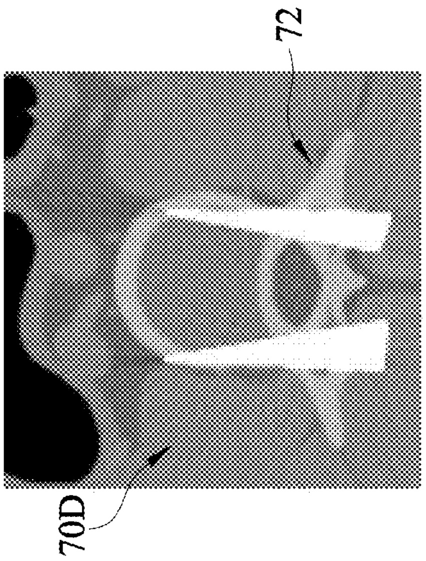

On the other hand, as shown in FIG. 5D, it shows a virtual monoenergetic image 70D imaged by the method S100 of the present disclosure for reducing metal artifacts in CT images. It not only effectively removes the metal artifacts in lumbar spine with bone screws area 72, but compared to FIGS. 5B and 5C, the normal tissue structure of the lumbar spine with bone screws area 72 is not removed, capable of improving the quality of spectral CT images.

Conclusively, the method for reducing metal artifacts in CT images of the present disclosure can generate the virtual monoenergetic CT images sof a specific energy (such as synchrotron radiation) through projection-based MD data of spectral CT and the monoenergetic image photon energy information to be obtained, capable of reducing the metal artifacts in CT images.

Furthermore, the present disclosure generates virtual monoenergetic images to reduce metal artifacts based on projection domain by means of image recombination rather than simply by means of image post-processing, which not only can effectively reduce metal artifacts, but can maintain normal tissue image structure information around high-attenuation material area.

In addition, the present disclosure can generate virtual monoenergetic CT images, and the pixel value in the image represents the attenuation coefficient of a specific energy photon (for example: 100 keV) in a certain area, thereby capable of more accurately representing the characteristics of the material in the area, which can improve the accuracy of image quantification.

Although the present disclosure has been disclosed as above in the form of embodiments, it is not intended to limit the present disclosure. Anyone with ordinary knowledge in the technical field may make slight changes and modifications without departing from the spirit and scope of the present disclosure, so the scope of protection of this disclosure shall be subject to the scope of the patent application attached.

What is claimed is:

1. A method for reducing metal artifacts in CT images, comprising the following steps:

a material decomposition (MD) calibration step, using multiple MD calibration phantoms with known characteristics and multiple spectral CT data corresponding thereto to construct a system characteristic model of spectral CT; and a MD testing step, comprising: the following steps:

imaging multiple testing objects with a different unknown material and thickness to obtain projection-based multiple spectral CT imaging data of different energy bins;

obtaining corresponding multiple basis material images of different materials based on projection data according to said spectral CT imaging data and said system characteristic model of spectral CT, and substituting said spectral CT imaging data and said system characteristic model of spectral CT into a basis MD algorithm in the step of obtaining corresponding multiple basis material images of different materials based on projection data according to said spectral CT imaging data and said system characteristic model of spectral CT; and combining said basis material images and a photon energy information to be recombined with each other to obtain multiple virtual monoenergetic images.

2. The method according to claim 1, wherein said MD calibration step comprises the following steps:

using multiple reference materials with known characteristics as said MD calibration phantoms; and imaging said MD calibration phantoms with a different material and thickness to obtain said spectral CT calibration data of different energy bins based on projection corresponding to said MD calibration phantoms with a different material and thickness.

3. The method according to claim 2, further comprising the following step:

placing said MD calibration phantoms between an X-ray tube and a photon-counting detector in the step of imaging said MD calibration phantoms with a different material and thickness.

4. The method according to claim 2, further comprising the following steps:

using said MD calibration phantoms as an input end of said system characteristic model of spectral CT;

using said spectral CT calibration data as an output end of said system characteristic model of spectral CT; and constructing said system characteristic model of spectral CT related to both said MD calibration phantoms and said spectral CT calibration data after the step of imaging said MD calibration phantoms with a different material and thickness.

5. The method according to claim 4, further comprising the following step: substituting said MD calibration phantoms together with said spectral CT calibration data corresponding thereto into a MD calibration algorithm to construct said system characteristic model of spectral CT in the step of constructing said system characteristic model of spectral CT related to both said MD calibration phantoms and said spectral CT calibration data.

6. The method according to claim 5, further comprising the following step: using a polynomial approximation method as said MD calibration algorithm in the step of substituting said MD calibration phantoms together with said spectral CT calibration data corresponding thereto into said MD calibration algorithm.

7. The method according to claim 5, further comprising the following steps:

adopting a maximum likelihood estimation method to estimate a MD calibration phantom calculation value; and using a error calibration look-up table to calibrate said MD calibration phantom thickness calculation value to obtain a material thickness estimation a calibration parameter for material calibration estimation in said system characteristic model of spectral CT in the step of substituting said MD calibration phantoms together with said spectral CT calibration data corresponding thereto into said MD calibration algorithm.

8. The method according to claim 1, further comprising the following step:

image-reconstructing said virtual monoenergetic image based on projection to obtain a three-dimensional CT reconstruction image after the step of obtain said virtual monoenergetic image.

* * * * *